US010080373B2

(12) United States Patent
Buwalda et al.

(10) Patent No.: US 10,080,373 B2
(45) Date of Patent: Sep. 25, 2018

(54) CREAM SUBSTITUTE

(75) Inventors: Pieter Lykle Buwalda, Groningen (NL); Arjen Sein, Leiden (NL)

(73) Assignee: COÖPERATIE AVEBE U.A., Veendam (NL)

( * ) Notice: Subject to any disclaimer, the term of this patent is extended or adjusted under 35 U.S.C. 154(b) by 630 days.

(21) Appl. No.: 12/518,362

(22) PCT Filed: Dec. 12, 2007

(86) PCT No.: PCT/EP2007/063825
§ 371 (c)(1),
(2), (4) Date: Nov. 5, 2009

(87) PCT Pub. No.: WO2008/071744
PCT Pub. Date: Jun. 19, 2008

(65) Prior Publication Data
US 2010/0143542 A1    Jun. 10, 2010

(30) Foreign Application Priority Data

Dec. 13, 2006 (EP) .................................... 06126035

(51) Int. Cl.
| A23L 1/0522 | (2006.01) |
| A23C 11/02 | (2006.01) |
| A23L 1/19 | (2006.01) |
| A23C 9/154 | (2006.01) |
| A23C 9/13 | (2006.01) |
| A23C 11/10 | (2006.01) |
| A23C 19/076 | (2006.01) |
| A23L 2/385 | (2006.01) |
| A23L 29/212 | (2016.01) |
| A23L 9/20 | (2016.01) |
| A23L 27/60 | (2016.01) |

(52) U.S. Cl.
CPC .......... *A23C 9/1542* (2013.01); *A23C 9/1307* (2013.01); *A23C 11/106* (2013.01); *A23C 19/0765* (2013.01); *A23L 2/385* (2013.01); *A23L 9/20* (2016.08); *A23L 9/22* (2016.08); *A23L 27/60* (2016.08); *A23L 29/212* (2016.08); *C12Y 204/01025* (2013.01); *A23V 2002/00* (2013.01)

(58) Field of Classification Search
CPC . A23L 1/05; A23L 1/0522; A23L 1/19; A23L 27/60; A23L 9/00; A23C 9/13; A23V 2002/00; A23V 2250/5118; A23B 2200/124
USPC ................................................... 426/61, 64
See application file for complete search history.

(56) References Cited

U.S. PATENT DOCUMENTS

| 2,086,184 | A | * | 7/1937 | Haas ................................ 426/62 |
| 5,104,674 | A | * | 4/1992 | Chen et al. .................... 426/573 |
| 5,120,561 | A | * | 6/1992 | Silva et al. .................... 426/531 |
| 5,153,020 | A | * | 10/1992 | Singer .................... A23C 20/00 426/567 |
| 5,275,837 | A | * | 1/1994 | Eastman ........................ 426/661 |
| 5,439,697 | A | * | 8/1995 | Gonzalez-Sanz ...... A23G 3/343 426/572 |
| 5,458,904 | A | * | 10/1995 | Zolper ................... A21D 2/183 426/573 |
| 5,686,132 | A | * | 11/1997 | Takaha ................ C08B 37/0009 426/590 |
| 5,711,986 | A | * | 1/1998 | Chiu et al. .................... 426/658 |
| 5,755,890 | A | * | 5/1998 | Yuan ........................ A21D 2/16 106/162.81 |
| 6,258,389 | B1 | * | 7/2001 | Adamany et al. .............. 426/34 |
| 6,864,063 | B2 | * | 3/2005 | Euverink ............. B01J 13/0065 127/32 |
| 9,615,587 | B2 | * | 4/2017 | Mastenbroek ........... A21D 2/02 |
| 2003/0190402 | A1 | * | 10/2003 | McBride .............. A23D 7/0053 426/601 |
| 2006/0099319 | A1 | * | 5/2006 | Stehouwer ........... A23C 9/1315 426/601 |
| 2010/0029928 | A1 | * | 2/2010 | De Vries ................ A61K 8/046 536/109 |
| 2011/0104354 | A1 | * | 5/2011 | Sein ........................ A21D 2/165 426/549 |

FOREIGN PATENT DOCUMENTS

| EP | 0 884 384 | 12/1998 |
| EP | 0 932 444 | 1/2002 |
| JP | 2000-316581 | 11/2000 |
| WO | 2006/062410 A1 | 6/2006 |

OTHER PUBLICATIONS

NPL 'Cream and Fat' retrieved on Jun. 30, 2011.*
NPL ATS Yogurt by Stephen Daniells 2008 retrieved from internet on Aug. 8, 2013.*
NPL Cream: in (http://theepicenter.com/ingredient/cream-types-of-cream-and-their-uses/).*
International Search Report for PCT/EP2007/063825, dated Jul. 9, 2008.
"Carbohydrates As Fat Replacers in Ice Cream", Confectionery Production, Specialised Publications Ltd., vol. 60, No. 2, (Feb. 1, 1994), pp. 122, 124, 159.
"Carbohydrates As Fat Replacers in Ice Cream", Confectionery Production, Specialised Publications Ltd., vol. 62, No. 9, (Sep. 1996), pp. 12-13.
Maarel Van Der, M.J.E.C. et al., "Amylomaltase From the Hyperthermophilic Bacterium Thermus Thermophilus: Enzyme Characteristics and Application in the Starch Industry", Mededlingen, vol. 3A, No. 65, (2000), pp. 231-234.
Van Der Maarel Marc J E C et al: "A novel thermoreversible gelling product made by enzymatic modification of starch", Starch: International Journal for the Investigation, Processing and Use of (Continued)

*Primary Examiner* — Bhaskar Mukhopadhyay
(74) *Attorney, Agent, or Firm* — McBee Moore Woodward & Vanik IP, LLC; Susan McBee; Chester Moore

(57) ABSTRACT

The present invention describes a food product comprising from 0.1 to 2.5 wt % of a starch which is treated with an amylomaltase.

10 Claims, No Drawings

(56) References Cited

OTHER PUBLICATIONS

Arbohydrates and Their Derivatives, vol. 57, No. 10, Oct. 1, 2015, pp. 465-472.

* cited by examiner

CREAM SUBSTITUTE

This application is the U.S. national phase of International Application No. PCT/EP2007/063825 filed 12 Dec. 2007, which designated the U.S. and claims priority to Europe Application No. 06126035.2 filed 13 Dec. 2006, the entire contents of each of which are hereby incorporated by reference.

This invention relates to the application of amylomaltase treated starch to substitute cream and/or fat in food products.

Today's consumers in modern societies are confronted with a disbalance between calorific intake and exercise. Therefore a growing percentage of the population is overweight and more and more people become obese. According to recent WHO figures (WHO 2003) 1 billion adults are overweight and 300 million are clinically obese. Obesity is connected to a broad spectrum of diseases such as cardiovascular diseases, type 2 diabetes etc. Therefore a growing need is obvious to reduce the intake of calories by replacing fat, sugar and other high calorie components of food products Moreover many products with fat contain a relatively high amount of saturated fatty acids that contribute to the melting characteristics of the product. However, the intake of such saturated fatty acids is also directly correlated with the occurrence of cardiovascular health diseases. A reduction in intake of saturated fatty acids is therefore recommended.

Over the past decades numerous patents have been filed where starch derivatives act as efficient replacers of fat in food products. For an overview see ("Carbohydrates used as fat replacers." Alexander, R. J. Editor(s): Alexander, Richard J.; Zobel, Henry F. Dev. Carbohydr. Chem. (1992), 343-70. Publisher: Am. Assoc. Cereal Chem). In general these starches are either acid- or enzyme-degraded starches or derivatives thereof. The functionality of the products are all derived from the fact that the starch derivatives form in the liquid food systems a continuous gel with specific particulate character. These particulates have a distinct disk shape character as described by Schierbaum and co-workers (Reuther, F.; Damaschun, G.; Gernat, C.; Schierbaum, F.; Kettlitz, B.; Radosta, S.; Nothnagel, A. Molecular gelation mechanism of maltodextrins investigated by wide-angle x-ray scattering. Colloid and Polymer Science (1984), 262 (8), 643-7). The amorphous phase of the gel is weak and under shear, in the mouth, the disks are loosened and perceived as fat droplets. Prerequisite for the function of the gel is that they are applied in concentrations where they do form gels, typically above 10% by weight.

A major draw back of the application of the degraded starches for use as a fat replacer is the high level of ingredient needed in order to achieve the desired fat mimicking properties. This means extra cost for food manufacturers, but, more importantly, limits the fat reducing possibilities, because the resulting product may have glue-like taste, because of the high level of starch derivative added. Moreover, although the caloric value of a product with such a high amount of starch can be lower than its full fat comparison, it still has a considerable caloric value.

Other starch derivatives that might be used in food products are chemically modified. Such chemical modification is usually unwanted.

In EP0932444 the production of alpha 1-4, alpha 1-4 glucosyltransferase (amylomaltase or EC 2.4.1.25) as well as the action of alpha 1-4, alpha 1-4 glucosyltransferase (amylomaltase or EC 2.4.1.25) on starch is described. "Alpha 1-4, alpha 1-4 glucosyltransferase" and "amylomaltase" will be interchangeable used in this text. This enzyme does not degrade the starch, but reattaches the amylose onto the amylopectin. The resulting product forms gels above 3% (w/w) solutions in water. These gels, although particulate in nature, have a texture normally connected to gums and other hydrocolloids and are different from gels of acid- or amylase-degraded or debranched products. The gels of amylomaltase-treated starch are thermoreversible at approximately 60° C. "Amylomaltase treated starch", "amylomaltase converted starch" and "amylomaltase modified starch" will be interchangeable used in this text, meaning that the starch is modified by amylomaltase activity. Preferably the enzymatic conversion (or modification or treatment) can be followed by means of reduction of the viscosity when the conversion takes place at 60-75° C. After the desired viscosity reduction has been reached, the conversion can be broken down (see EP0932444).

An example of the production of amylomaltase treated starch is described in EP0932444. The amylomaltase treated starch can be prepared from suspension of potato starch in water (19-20% w/w). This suspension is jet-cooked at 150-160° C. in order to dissolve the starch. The product is cooled in vacuo to 70° C. Flash cooling is a preferred option. The pH is adjusted to 6.2 using for example 6N $H_2SO_4$. Then amylomaltase (2 ATU/g starch) was added. The solution was stirred for 2 to 20 hr at 70° C. Then the solution was jetcooked at 130° C. for a short time, for example 1 to 20 seconds and spray dried using for example a model Compact spray dryer (Anhydro, Danmark).

Surprisingly it has now been found that by employing amylomaltase treated starches well below the concentration where they form a continuous gel, a good replacer for fat and/or cream is obtained in many food products such as dairy products, soy-protein based products such as soy-based drinks and desserts, dressings and mayonnaises. In general these food products have a high water content, for example 60 wt % or more of the product is water.

Dairy products encompass a wide range of products: fermented products such as yogurt, curd and cheese, RTE desserts, etc. etc. For yogurt three generic types of yogurt are considered: set yogurt, stirred yogurt and drinking yogurt. By dairy products is meant products which comprise for a substantial part of the milk ingredients, for example the protein contents of these products is for at least 50 wt %, preferably at least 70 wt %, of milk protein ingredients including milk, whey, casein, hydrolysates and ferments thereof.

The microstructural role of fat globules in food products can be envisaged as firstly building consistency in the finished products, and secondly upon consumption, that is breakdown in the mouth, melting of the fat in the globules, resulting in weakening and yielding of the structure. Amylomaltase-treated starch behaves in the same way. It forms discrete gel domains (a discontinuous phase) in for instance a dairy-based product like yogurt, hence contributing substantially to the consistency of the food product. Upon oral breakdown, these discrete domains melt and the overall structure yields.

In this way humans perceive products with amylomaltase treated starch as creamy as the product with fat. And since the amount of starch needed to replace a certain quantity of fat is equal or lower than the amount of fat, a total reduction in calorie content is obtained, as well as a reduction of unwanted saturated fatty acid intake.

The discrete domains can easily be observed by light microscopy. In a yogurt-type product the protein phase appears as contrastfull irregularly-shaped flocs of particles, particles individually being close to the resolution limit of the light microscope (ranging from around a few microns to smaller than 1 micron). Next to that the amylomaltase-treated starch domains are seen as lighter smoothly shaped particles, not as contrast full as the protein flocs. Typical sizes as seen by light microscopy are in the range of 5-20 micron.

Confocal Scanning Laser Microscopy (CSLM) illustrates products in more unperturbed setting than in conventional light microscopy. A similar picture emerges by CSLM for a yogurt-based product. When the protein phase is stained, this phase appears as the continuous phase, leaving holes of a discontinuous phase without any stain. These are the discontinuous enzyme-treated starch domains which are 5-15 micron large. Such voids are generally not seen in CSLM images of non-fat yogurt Common polymer physics theory predicts the phase separation of protein/polysaccharide mixtures. In more general wording any two type of polymers demix, either in bulk or in solution, unless the two polymer types show specific interactions. Therefore phase separation alone already induces formation of discrete domains of amylomaltase-treated starch in a protein phase. However, locally—within a domain—the concentration of amylomaltase-treated starch is so high that that domains acts as a gel particle with the same melting characteristics as is found for a macroscopic gel of the specific starch.

Without being bound by any theory the inventors believe that the gel is caused by small crystalline regions formed by the long branches of the amylopectin molecules that were made extra long through the enzyme treatment. These crystalline regions act as physical crosslinks between the starch molecules. Melting is caused by thermal dissolution of these small crystalline domains. It is moreover believed that the formation of the small crystalline domains stimulates the phase separation: starch molecules are thermodynamically driven to form associates.

Many hydrocolloids in food products thicken the continuous aqueous phase. In set or stirred yogurt for instance, hydrocolloids such as gelatin, chemically modified starch and maltodextrins make the serum phase more viscous. This results in an overall higher product viscosity and that has a certain positive contribution to oral perception. We have found now that the formation of discrete domains of amylomaltase-treated starch in such a yogurt-type product is however a closer mimic of the textural contribution of fat globules in oral perception than thickened serum phase by hydrocolloids.

Also in acidified milk drinks and drinking yogurts, the role of amylomaltase-treated starch is found to be close to the contribution of fat globules. The discrete domains of amylomaltase-treated starch are caught in the protein flocs that occur upon acidification, just like fat globules do. Other hydrocolloids that are commonly used in this type of drinks, such as pectins, stabilise the protein flocs colloidally. Such hydrocolloids remain in the continuous serum phase in between the protein flocs and thereby prevent serum separation.

Parallel to domain formation in protein-starch mixtures, this can also occur between amylomaltase-treated starch and other polysaccharides, such as galactomannans (such as xanthan gum, locust bean gum, guar gum), but also for other starches, native or chemically modified.

Therefore the fat replacing effect can also be seen in food products that are made from mixtures of polysaccharides and amylomaltase-treated starch when the latter indeed is present in a level below 3%. Typical examples for such products can be found in the dressings and mayonnaise area.

Yogurt production generally begins with raw and processed milk products. Milk products such as whole, reduced fat, skim, condensed, or dry milk may be used. Generally bovine milk is used, though yogurt may also be produced from the milk of other mammals, such as goats or sheep. Soy or nut milks can also be added to or substituted for animal milk mixtures to produce yogurt products.

Non-fat yogurt production begins in general by blending non-fat dry milk powder with non-fat milk and with a mixture of vitamins such as vitamins A and D. After suitable hydration of the non-fat dry milk powder occurs, usually after a period ranging from about 30 minutes to 2 hrs, the milk mixture is preheated and homogenized. The resulting mixture is then pasteurized, for example at a temperature of about 90° C. for approximately 6 to 7 minutes.

Preferably the optional hydrocolloids and thinkeners can be added to the premix before pasteurisation. The amylomaltase treated starch is preferably added before pasteurisation.

The pasteurized milk mixture is then cooled to a temperature suitable for fermentation by lactose metabolizing bacteria.

The cooled milk mixture is inoculated with appropriate strains of bacteria, such as *Lactobacillus bulgaricus* and *Streptococcus thermophilus*. Other strains of lactose-fermenting bacteria may also be added, such as *Lactobacillus acidophilus* or *Lactobacillus bifidus*, to assist in the fermentation or provide probiotic properties to the final beverage.

To augment the probiotic properties of the yogurt-based beverage *Lactobacillus casei* may be added. Other probiotic microorganisms which may be added either during or after fermentation include *Lactobacillus gasseri, Lactobacillus plantarum, Lactobacillus johnsonii, Lactobacillus reuteri, Lactobacillus rhamnosus, Bifidobacterium bifidum, Bifidobacterium lactis, Bifidobacterium longum, Bifidobacterium breve, Bifidobacteriuminfantis, Enterococcus faecium, Enterococcus faecalis*, and *Streptococcus salivarius* or the yeast *Saccharomyces boulardii*.

The inoculated milk culture is maintained under conditions favoring curd formation and thus allowed to ferment without substantial agitation. Generally, the fermentation temperature is kept within the range of 30-45° C.

When the mixture reaches a pH ranging from about 4.4 to 4.6, usually, about 4.55, it is agitated and cooled to slow or stop the initial fermentation.

The resulting stirred yogurt base product is then cooled to about 2 to 7° C., preferably about 4° C. and optionally filtered to remove lumps, for instance, by passage through a ⅛ inch wire mesh filter.

The yogurt base product, or white mass, may then be stored at a reduced temperature for 10-15 hours, e.g., at 4° C.

The product of the invention may further comprise mixing of conventional food additives into the dairy based yogurt. Additives, such as acidulants, antioxidants, bulking agents, bulking sweeteners, colorants, dietary fiber, emulsifiers, enzymes, fat replacers, flavors, flavor enhancers, gases, preservatives, non-nutritive sweeteners, or processing aids which may be added to consumable foods and beverages are known in the art and are described by the Kirk-Othmer Encyclopedia of Chemical Technology, 4th edition, vol. 11, "Food Additives", pages 805-833, which is incorporated by reference. For example, natural sweeteners, such as sucrose, dextrose, or fructose, or artificial sweeteners, such as aspartame, sucralose, saccharin, cyclamate, acetsufame K, alitame, glycyrrhizin, stevioside, or thaumatin may be added. Addition of other food items such as fruit preparations can also be added.

Full fat and low-fat yogurt are produced in essentially the same way.

The resulting yogurt base with full fat yogurt constitutes a weak gel. For low-fat and non-fat yogurt thickeners and gelling agents such as modified starches and gelatin are added in order to obtain a weak gel. Without further processing these yogurts are referred to as set yogurts.

To convert these yogurts into stirred yogurts the resulting mass is transferred through a stirring processing resulting in a yogurt that is pourable. The stirring process can be performed in coolers, stirrers, pressureless homogenisers, etc.

To convert the set yogurts into drink yogurts the set yogurts are passed through a homoginesizer or a high speed mixing device. The resulting yogurt has a relatively low viscosity allowing drinking out of a cup, or another suitable packaging.

The addition of thickeners and gelling agent to low- and non-fat yogurts is by no means straightforward. In the process industry numereous processes have been developed. The skilled person in the art of a given food manufacturer is familiar to work with these additives and ingredients.

A major draw back of low- and non-fat yogurt is their lack of creamy taste. Partly this can be repaired by adding a gelling agent and or a modified starch. However, this still will impair dry and acid taste.

In the present invention amylomaltase treated starch is added to a food product in order to improve the creamy taste.

As stated earlier amylomaltase reattaches the amylose in parts to the amylopectin, yielding a chain elongated amylopectin. Suitable starches for the preparation of amylomaltase treated products are cereal starches such as corn, wheat, rice, barley, rye or other cereal starches, root and starches such as tapioca, sweet potato and arrow root and potato starch and leguminous starches such as pea and bean starches. Preferably amylomaltase treated potato starch is used in the present invention. Also suitable are starches with elevated amylose level such as high amylose corn starch, wrinkeled pea starch etc. It can be envisaged that blends of starches with elevated amylose levels and the so-called waxy starches such as waxy corn, waxy barley, waxy wheat, waxy tapioco, waxy rice and waxy potato starches will yield satisfactory product too. It is understood that starches that are slightly modified before or after amylomaltase treatment will produce good products too. It is understood that the present invention can also be carried out using slightly modified starch. Modifications are well known to those skilled in the art and can be achieved using acid conversion, thermal treatment, cross-linking, esterification, etherification, enzymatic modification oxidation etc.

The invention will now be demonstrated with the following non restrictive examples.

EXAMPLES

General

One Amylo Maltase unit (ATU) is defined as the amount of amylomaltase which produces 1 µmol of glucose per minute under the assay conditions of the test.

Assay:

Amylomaltase is incubated with maltotriose at pH 6.50 and 70° C., releasing glucose from the substrate. The incubation is stopped by adding hydrochloric acid. The amount of released glucose is a measure for the amylomaltase activity and is examined using a glucose test assay (NADH formation) on a Selectra analyzer at a wavelength of 340 nm.

Example 1

Full Fat Set Yogurt

Standardised and homogenized (200/20 bar) milk was used to produce a set 5% yogurt in an industrial relevant manner. A dry mix (sugar (Suiker Unie, Breda) and amylomaltase modified potato starch were added to the milk and allowed to hydrate during 15 minutes. The milk was pasteurised (10 minutes at 90° C.) and cooled to fermentation temperature (42° C.). After inoculation of the milk with 0.05% (m/m) ISt (CSK Food Enrichment, Leeuwarden) and addition of 0.06% (m/m) flavour (strawberry flavour COST 921), the inoculated milk was filled into 125 ml cups, sealed and allowed to ferment during 5-6 hours at 42° C. After reaching pH 4.5 the cups were cooled and stored at 4° C.

A sensory analyses showed a 30% increase in creamy taste as compared to a standard 5% fat yogurt without the amylomaltase modified starch

Example 2

Non-Fat Stirred Yogurt

Skimmed milk (0% fat) was used to produce stirred yogurt in an industrially relevant way. To the skimmed milk 5% sugar (Suikerunie Breda), 0.35% amylomaltase modified potato starch, 1.4% of modified waxy maize starch (Thermflo, National Starch) and 1.1% of whey protein concentrate. The milk and the dry ingredients were allowed to hydrate for 15 minutes. The mixture was heated to 65° C. and subsequently homogenized at 80 bar. The resulting product was pasteurized at 93° C. for 6 minutes. Then the product was cooled to 43° C. and 0.05% (m/m) ISt (starter culture CSK Food Enrichment, Leeuwarden) were added. The product was incubated at 43° C. for 5-6 after which the pH was 4.5. The product was gently whisked with a mechanical stirred until smooth, cooled to 20° C. and filled in beakers. After refrigeration for one night at 4° C. the product was tested by a sensory panel. In a reference experiment the 0.35% amylomaltase modified starch was replaced by 0.35% gelatin (240 bloom, Sobel Industries, hereafter Reference).

In the sensory evaluation the product containing amylomaltase modified starch showed a 50% increase in creaminess as compared to the Reference containing gelatin.

Example 3

Drink Yogurt

A dry mix of 10 wt % sugar (Suiker Unie, Breda, the Netherlands) and amylomaltase modified potato starch (0.5 or 0.7 wt %) was added to standardised and homogenised (200/20 Bar) milk (fat levels of 0, 1 or 2 wt %) and allowed to hydrate during 15 minutes. The milk was pasteurised for 10 minutes at 90° C. and cooled back to fermentation temperature (32° C.). After inoculation with 0.001% yogurt culture (Ist, CSK Food Enrichment, Leeuwarden, the Netherlands), the milk was allowed to ferment during 16 hours at 32° C. After reaching pH 4.5, the yogurt was stirred and homogenised, filled in 0.5 L PE beakers, sealed, cooled and stored at 4° C. until further analysis. The viscosity of the products was determined using a so-called Posthumus funnel, the results are combined in the following table.

| Product number | % Fat | % amylomaltase modified starch | Posthumus viscosity (seconds) |
|---|---|---|---|
| 1 | 0 | 0.5 | 6 |
| 2 | 0 | 0.7 | 7 |
| 3 | 1 | 0.5 | 7 |
| 4 | 1 | 0.7 | 8 |
| 5 (reference) | 2 | 0 | 6 |

The products were also assessed by a sensory panel. A clear ranking for several attributes was seen: increased richness/creaminess/softness/smoothness and reduced powdery/dissolving was determined by the panel, in ascending order: 5 (reference) equal to product 1-product 2-product 3-product 4.

Example 4

Soy-Milk-Based Dessert

A soy-milk-based, yogurt-style dessert was made in the following way. 4 wt % of sugar and a quantity of amylomaltase modified potato starch (0, 0.5 or 1.0 wt %) were mixed into a commercial pasteurised soy milk (Alpro Soya Drink Natural Fresh—with mild vanilla aroma). This mix was heated to 85° C. for 30 minutes, and then cooled down to 42° C., inoculated with a yogurt culture (Delvo-Yog CY340, DSM Food Specialties, Delft, the Netherlands). After 7 hours the pH had reached a value of 4.6. The fermented product was broken down by passing through a high pressure homogeniser (Rannie LAB 12,50H) at 0 Bar, and filled in pots. After 5 days the viscosity of the three products was assessed (Brookfield viscometer, spindle TB, 30 rpm, helipath method, value taken at 25 mm depth) and a sensory evaluation was performed. Results are given in the table below.

| % amylomaltase-treated starch | Brookfield Viscosity (Pa · s) | Sensory evaluation |
|---|---|---|
| 0 | 2.5 | strong sweet vanilla taste, with a slight taste of beans; rough but quite liquid, homogenous mouth feel |
| 0.5 | 3.2 | sweet vanilla taste, with less bean-flavour and a bit more viscous, but still homogenous mouth feel |
| 1.0 | 4.1 | less sweet vanilla taste with even less bean-flavour and a quite viscous thickening mouth feel |

Example 5

Low Fat Cream Cheese

Cream cheese was prepared by mixing commercial zero-fat fresh cheese (quarg) with full fat cream (containing 40.3% fat), salt, 0.2% Locust Bean Gum (Grindsted LBG 147—Danisco) and 0.05% Carrageenan (Carrageen CL340C—Danisco) and amylomaltase treated potato starch at 60° C., in levels as indicated in the table. This mixture further heated to 85° C. and left there for 15 minutes and then cooled back to 75-80° C. and homogenised with a high pressure homogeniser operating at 150/30 Bar and subsequently hot filled (65-70° C.) in cups. The products were stored cold (4-7° C.) until further characterisation.

| Composition Cream cheese products | | |
|---|---|---|
| | Reference Cream cheese 12% fat | Product 1 Cream cheese 7% fat |
| Fresh cheese (10% protein, 0% fat) | | 79 |
| Fresh cheese (12% protein, 0% fat) | 64 | |
| Cream | 30 | 17 |
| Amylomaltase-modified starch | 0 | 2 |
| Locust bean gum/carrageenan blend | 0.25 | 0.25 |
| Salt | 0.3 | 0.3 |
| Water | 5.9 | |

In a small test panel the product 1 (with 2% amylomaltase-treated starch and 7% fat) was scored almost equally creamy as the reference (12% fat, no starch). Also the spreadability of both products was comparable.

The products were also observed by light microscopy and domains of amylomaltase-treated starch were clearly visible. These domains were spherical and typically in the order of 10-40 μm.

Example 6

Low Fat Cream Cheese 0.85% amylomaltase-treated potato starch was added to milk (3.5% protein, 2.8% fat and 4.7% carbohydrates). The mixture was pasteurised for 5 minutes at 85° C., allowed to cool to 22° C. and inoculated with a starter culture (Probat 505 FRO, Danisco). The product was allowed to acidify to pH 4.7, which took approximately 20 hours. The curd was cut and stirred and the whey was separated from the curd by a 10kD Ultrafiltration step.

This concentrated acidified milk product was heated to 60-65° C., subsequently 0.25% of a hydrocolloid blend (0.2% Locust Bean Gum (Grindsted LBG 147—Danisco) and 0.05% Carrageenan (Carrageen CL340C—Danisco)) and 0.3% salt was added, further mixed at 85° C. for 15 minutes and then cooled back to around 75° C. and homogenised by a high pressure homogeniser on 150/30 Bar. Then the product was filled hot (65° C.) into containers and stored cold (4-7° C.) until further characterisation. The product contained 8% protein, 7.5% fat, and 2% of amylomaltase-treated starch. No starch was seen in the drained off whey, determined by iodine staining of the whey.

The product was perceived well spreading and had a good creaminess. Observed by light microscopy the product displayed small spherical domains typically of 1-10 μm.

Example 7

Skimmed Milk with "Full Fat" Mouth Feeling

Amylomaltase-treated potato starch was added to warm skim milk (at least 65°) and stirred for 5 minutes and then stored cool overnight. The sample showed small non-spherical domains of 20-40 μm in size. These domains were absent in skim milk that was treated in the same way, without the starch.

In another experiment amylomaltase-treated potato starch was added in increasing concentration to skim milk and heated to at least 85° C. These samples were observed by confocal scanning laser microscopy. Here it was clear that separate domains of amylomaltase-treated starch phases in water are seen between the protein. Only when the amylomaltase-treated starch concentration increases to higher than 3%, the starch is seen to create its own volume-spanning network.

In addition a coffee-flavoured milk drink was made by first boiling milk in the microwave and then mix in the ingredients as given in the below table. In Composition A (with amylomaltase-treated potato starch) the powders were mixed while stirring, and stirring was continued for 5 minutes. At the end the temperature was 74.5° C. For Composition B the powders were added to the boiled milk and shaken well with the lid covered. Both products were kept overnight and tasted next day.

| Composition | A | B |
|---|---|---|
| Milk | 72.2 gram | 73.5 gram |
| Amylomaltase-treated starch | 0.80 gram | 0 |
| Instant coffee | 0.90 gram | 0.89 gram |
| Sugar | 4.87 gram | 4.85 gram |

Instant coffee: Douwe Egberts Aroma Rood Oploskoffie (Instant coffee)

Sugar: Euro Shopper—Albert Heijn

The amylomaltase-treated potato starch-containing sample was considered creamier and fuller by a small test panel.

Example 8

Zero-Fat Dressing

A zero-fat dressing type water phase was made in the following way: 0.5% amylomaltase-treated potato starch and 0.5% guar (Danisco Grindsted Guar) were dissolved in hot water (80° C.) at pH 4.5. After stirring this dispersion for 10 minutes it was allowed to cool and was stored cool (4-7° C.). After 1 week 2 layers were formed, of about equal volume. The upper half was almost clear, the bottom phase was turbid. By light microscopy it was shown that the lower phase contained many spherical domains of amylomaltase-treated starch. The domain size ranged from below 1 to over 75 μm.

The invention claimed is:

1. A process of forming a discontinuous phase formed by discrete gel domains in a food product having a continuous protein phase, which food product is a soy-based product, a dessert, a dressing, a mayonnaise, or a dairy product, said process comprising adding amylomaltase EC 2.4.1.25-treated starch consisting of chain-elongated amylopectin to said food product in an amount from 0.1 to 2% w/w, wherein said starch is present as discrete domains of concentrated amylomaltase-treated starch of from 5 to 20 μm, and wherein said starch does not form a volume-spanning network.

2. The process according to claim 1, wherein the starch which is treated with an amylomaltase EC 2.4.1.25 is a fat substitute in the food product.

3. The process according to claim 1, wherein the amylomaltase EC 2.4.1.25-treated starch is used as cream substitute.

4. The process according to claim 1, wherein the food product is yogurt.

5. The process of claim 1, wherein the discrete gel domains contain regions of crystalline starch.

6. The process of claim 1, wherein the food product contains 50 wt% to 70wt% protein.

7. A food product which is a dairy product, a soy-protein based product, a dessert, a dressing, or a mayonnaise, which food product comprises of from 0.1 to 2.0wt. % of amylomaltase(EC 2.4.1.25)-treated starch, which starch is present as a discontinuous phase consisting of discrete gel domains of from 5 to 20 μm of concentrated amylomaltase-treated starch within a continuous protein phase, wherein the starch consists of chain-elongated amylopectin, and wherein said starch does not form a volume spanning network.

8. The food product according to claim 7, wherein the amylomaltase-treated starch is a cream substitute in the food product.

9. The food product according to claim 7 which is yogurt.

10. The food product according to claim 7, wherein the food product is a low-or non-fat food product.

* * * * *